United States Patent [19]

Nambu

[11] Patent Number: 4,923,459
[45] Date of Patent: May 8, 1990

[54] STEREOTACTICS APPARATUS

[75] Inventor: Kyojiro Nambu, Tochigi, Japan

[73] Assignee: Kabushiki Kaisha Toshiba, Kawasaki, Japan

[21] Appl. No.: 243,921

[22] Filed: Sep. 13, 1988

[30] Foreign Application Priority Data

Sep. 14, 1987 [JP] Japan ................................ 62-228605

[51] Int. Cl.$^5$ ............................................. A61B 19/00
[52] U.S. Cl. .................................................... 606/130
[58] Field of Search ............ 128/303 B, 660.1, 653 R, 128/653 A, 660.07; 606/130

[56] References Cited

U.S. PATENT DOCUMENTS 4,608,977  9/1986  Brown ............................. 128/303 B
4,617,925 10/1986  Laitinen .......................... 128/303 B

FOREIGN PATENT DOCUMENTS 18166 10/1980 European Pat. Off. .

OTHER PUBLICATIONS

H. Requardt, et al., "Electromedica 55", *Helmholtz Coils In Nuclear Spin Tomography*, Issue 2, pp. 61–67 (1987).

Primary Examiner—Michael H. Thaler
Attorney, Agent, or Firm—Foley & Lardner, Schwartz, Jeffery, Schwaab, Mack, Blumenthal & Evans

[57] ABSTRACT

A stereotactics apparatus comprises a frame fixed on a head of a patient and a marker member fixed on the frame. The frame has a frame coordinate system within which the head and the marker member are located. The marker member is tomographically imaged together with the head by a tomographic imaging apparatus (e.g. MRI apparatus), and is displayed as marker image together with the tomographic image of the head. The coordinate system is reconstructed on the basis of the displayed marker image, so that coordinates of the surgical target are calculated on the basis of the reconstructed coordinate system. The marker member is located on an imaginary curved surface having a concave shape toward the head and located on the frame. Thus, the marker member is located at angular position such that all portions of the marker member are equidistantly away from a center of magnetic field. Therefore the marker member can be located comparatively near the center. Since the nonuniformity of the magnetic field intensity is minimized at a position closer to the center, the marker image distortion is suppressed, thus reducing the positional deviation of the marker image. Therefore, the coordinate system can be accurately reconstructed on the image, and hence the coordinates of the surgical target can be accurately calculated.

15 Claims, 8 Drawing Sheets

STEREOTACTICS APPARATUS

BACKGROUND OF THE INVENTION

1. Field of the Invention

The present invention relates to a stereotactics apparatus for designating the position of a portion of interest for a surgical operation in stereotaxy on the basis of a tomographic image of a predetermined portion of a patient which is obtained by a tomographic imaging apparatus.

2. Description of the Related Art

Stereotaxy is a surgical operation for removing, destroying or discharging a portion affected by an ailment such as a cerebral tumor in nuerosurgical clinics. A position of an ailment (i.e., a surgical target) within a brain is calculated in the form of three-dimensional coordinates on the basis of a tomographic image obtained by tomography. For example, a probe is inserted into the ailment to destroy the portion affected by the ailment.

Figure 1:
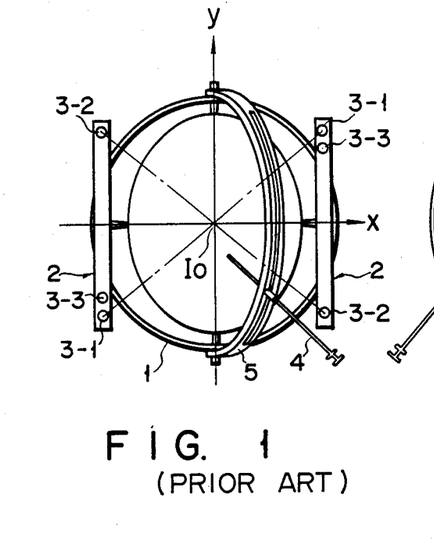
FIG. 1 is a front view of the apparatus and FIG. 2 is a side view of the apparatus.
Figure 2:
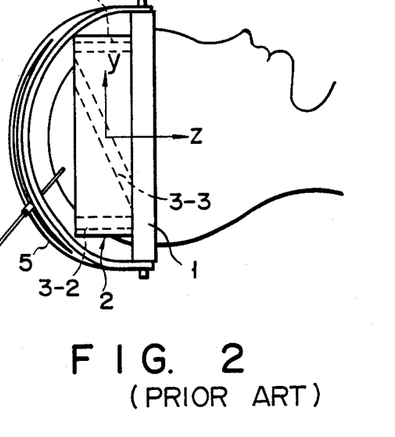

FIGS. 1 and 2 show one example of conventional stereotactics apparatuses. As shown in FIGS. 1 and 2, a stereotactics apparatus includes frame 1 fixed on a head of a patient and two gauge receptacles 2 fixed on the frame. Marker members 3 (3-1, 3-2 and 3-3) are arranged in each gauge receptacle 2 and are displayed as marker images together with a tomographic image of the head. An operational tool consisting of probe 4 and arc 5 for positioning probe 4 is mounted on frame 1.

This apparatus has frame coordinate system $(x,y,z)$ defined on frame 1. A surgeon inserts probe 4 into surgical target T on the basis of coordinates $(x_0,y_0,z_0)$ of surgical target T in the frame coordinate system. As an example, origin $I_O$ of the frame coordinate system is defined as an intersection between a line connecting marker members 3-1 of both receptacles 2 and a line connecting marker members 3-2 of both receptacles 2. The x-, y-, and z-axes are defined a shown in FIGS. 1 and 2.

Figure 3:
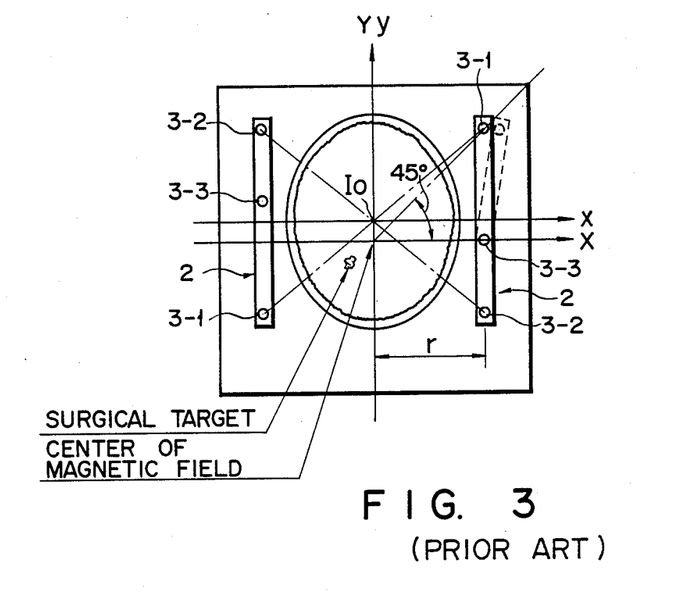
FIG. 3 is a view showing an image including a tomographic image of a head and marker images (prior art)

A tomographic image (slice image perpendicular to the z-axis) of the head is obtained by the tomographic imaging apparatus and is displayed as an image, as shown in FIG. 3. This image has an image coordinate system $(X,Y,Z)$. Coordinates $(X_0,Y_0,Z_0)$ of surgical target T in this image coordinate system can be obtained from the image. However, the image coordinate system does not match the frame coordinate system. Therefore, the correspondence between the image coordinate system and the frame coordinate system must be established. More specifically, the frame coordinate system must be defined on the image. For this purpose, marker members 3 on gauge receptacles 2 are utilized.

Marker members 3 are tomographically imaged together with the head and are displayed as marker images 3 together with a tomographic image of the head. The positional relationship between the tomographic image of the head and the marker images is the same as that between the head and the marker images. For this reason, the frame coordinate system $(x,y)$ is reconstructed (reconstruction along the z-axis will be described later in an embodiment) on the image on the basis of the marker images 3 in the same procedures as in setting of the frame coordinate system. Therefore, coordinates $(x_0,y_0)$ of surgical target T are calculated by measurement with a scale on the basis of the reconstructed frame coordinate system. The surgeon can insert probe 4 into surgical target T on the basis of the calculated coordinates.

A magnetic resonance imaging (MRI) apparatus is used as a tomographic imaging apparatus. A point having zero intensities of X-, Y-, and Z-axis gradient fields is defined as the center of the magnetic field. As shown in FIG. 3, (gradient field coordinate system) = (image coordinate system) = $(X,Y,Z)$ is established.

Nonuniform distributions of intensities of static and gradient fields occur at portions away from the center of the magnetic field. The intensity of the static field must be uniform, but is actually nonuniform. The intensity of each gradient field must have linear characteristics i.e., must be in proportion to the position of the corresponding gradient field axis, but is distorted. For these reasons, the intensity of the magnetic field (i.e., static field intensity + each gradient field intensity) does not have linear characteristics i.e., is not in proportion to the position of each gradient field axis, and is distorted. As a result, a reconstructed image is distorted and is often deviated from a position at which the image is theoretically displayed.

The degree of nonuniformity of the magnetic intensity distribution is increased at a position away from the center of the magnetic field. In a conventional stereotactics apparatus, gauge 2 is flat, as shown in FIG. 1. That is, marker members 3 are placed on a flat imaginary plane. For this reason, as shown in FIG. 3, the distances between the center of the magnetic field and marker images 3-1, 3-2 and 3-3 are different from each other. A marker image relatively separated from the center of the magnetic field is distorted greater than that located near the center of the magnetic field and is displayed with a larger positional error. That is, a positional error of the marker image occurs.

The degree of nonuniformity is proportional to the power of 4 to 5 of the radius from the center of the magnetic field. Distortions of two marker images 3-1 and 3-3 on the right side of FIG. 3 are compared. If a distance between marker image 3-3 and the center of the magnetic field is given as r, a distance between marker image 3-1 and the center of the magnetic field is given as $\sqrt{2}r$ (an angle defined by marker image 3-3, the center of the magnetic field, and marker image 3-1 is given as 45°). For this reason, marker image 3-1 is distorted by $(\sqrt{})^n$ times with respect to marker image 3-3 (n = 4 to 5). As a result, the positional error of marker image 3-1 is figured to be $(\sqrt{2})^n$ times that of marker image 3-3. For example, marker image 3-1 is deviated, as indicated by a dotted line in FIG. 3.

The marker image positional error does not allow accurate reconstruction of the frame coordinate system. Coordinates of the surgical target in the frame coordinate system cannot often be accurately calculated.

When an X-ray CT is used as a tomographic imaging apparatus, the following problem occurs. A image is displayed on a circular screen in the X-ray CT apparatus due to its structural limitations. In addition, the tomographic image is an enlarged or reduced image.

Figure 11:
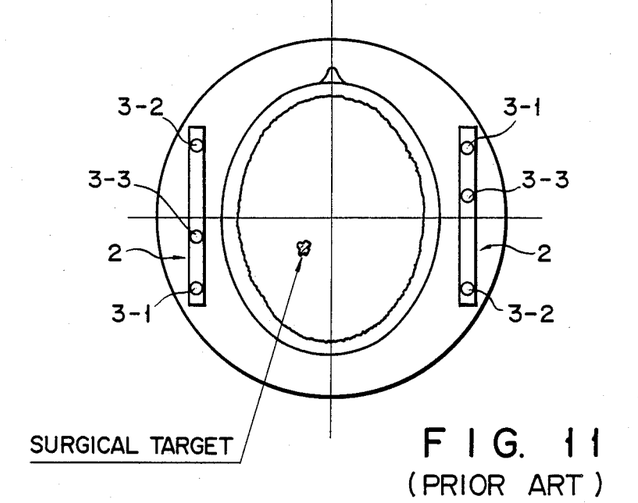
FIG. 11 shows the image based on the conventional technique and FIG. 12 shows the image based on the present invention.

In order to precisely display the tomographic image, the tomographic image is preferably displayed as an enlarged image as large as possible. In order to reconstruct the frame coordinate system, marker images must be displayed on the screen. For this reason, a magnification is preset such that marker images 3 are displayed near the peripheral edge of the screen, as shown in FIG. 11.

However, in the conventional stereotactics apparatus, marker members are located on the flat imaginary plane. For this reason, a space for marker images 3 must be sufficiently assured between the tomographic image of the head and the peripheral edge of the screen. The magnification of the image must be inevitably small. The tomographic image of the head and the marker images are displayed on the screen in a relatively small size. Precision of the tomographic image of the head is insufficient. In addition, the marker images are displayed in a relatively small size, and the marker images on the screen cannot be accurately read. As a result, the frame coordinate system cannot be accurately obtained.

SUMMARY OF THE INVENTION

It is a first object of the present invention to provide a stereotactics apparatus capable of accurately reconstructing a frame coordinate system on an image and accurately calculating coordinates of a surgical target.

It is a second object of the present invention to provide a stereotactics apparatus capable of suppressing positional errors of marker images by suppressing distortion of the marker images when a tomographic image is photographed by an MRI apparatus.

It is a third object of the present invention to provide a stereotactics apparatus capable of precisely displaying a tomographic image when the tomographic image is photographed by an X-ray CT apparatus.

According to the present invention, there is provided a stereotactics apparatus which utilizes tomographic imaging means for photographing a predetermined portion of a patient to display a tomographic image of the predetermined portion so as to designate a surgical target of the predetermined portion on the basis of the tomographic image, comprising:

frame means having a frame coordinate system and fixed in the predetermined portion such that the predetermined portion is located within the frame coordinate system; and means for calculating coordinates of the surgical target in the frame coordinate system, the calculating means being provided with a marker member, the marker member being fixed on the frame means so that the marker member is adjacent to the predetermined portion and located within the frame coordinate system, the marker member being tomographically imaged together with the predetermined portion by the imaging means and being displayed as marker image together with the tomographic image of the predetermined portion, whereby the frame coordinate system is reconstructed on the basis of the displayed marker image, so that the tomographic image of the predetermined portion is located within the reconstructed frame coordinate system and coordinates of the surgical target are calculated on the basis of the reconstructed frame coordinate system, wherein the frame means includes an imaginary curved surface having a concave shape toward the predetermined portion, and the marker member is located on the imaginary curved surface.

The marker member according to the present invention is located on an imaginary curved surface having a concave shape toward a predetermined portion of a patient. For this reason, when a tomographic image is obtained by the MRI apparatus, the marker member is located at an angular position such that all portions of the marker member are equidistantly spaced away from the center of the magnetic field. For this reason, as compared with the conventional case wherein the marker members are located on the flat imaginary plane, the marker member can be located near the center of the magnetic field. Since the nonuniformity of the magnetic field intensity is minimized at a position closer to the center of the magnetic field, the marker image distortion is suppressed greater than that in the conventional stereotactics apparatus, thus reducing the positional error of the marker image. Therefore, the frame coordinate system can be accurately reconstructed on the image, and hence the coordinates of the surgical target can be accurately calculated.

Figure 10:
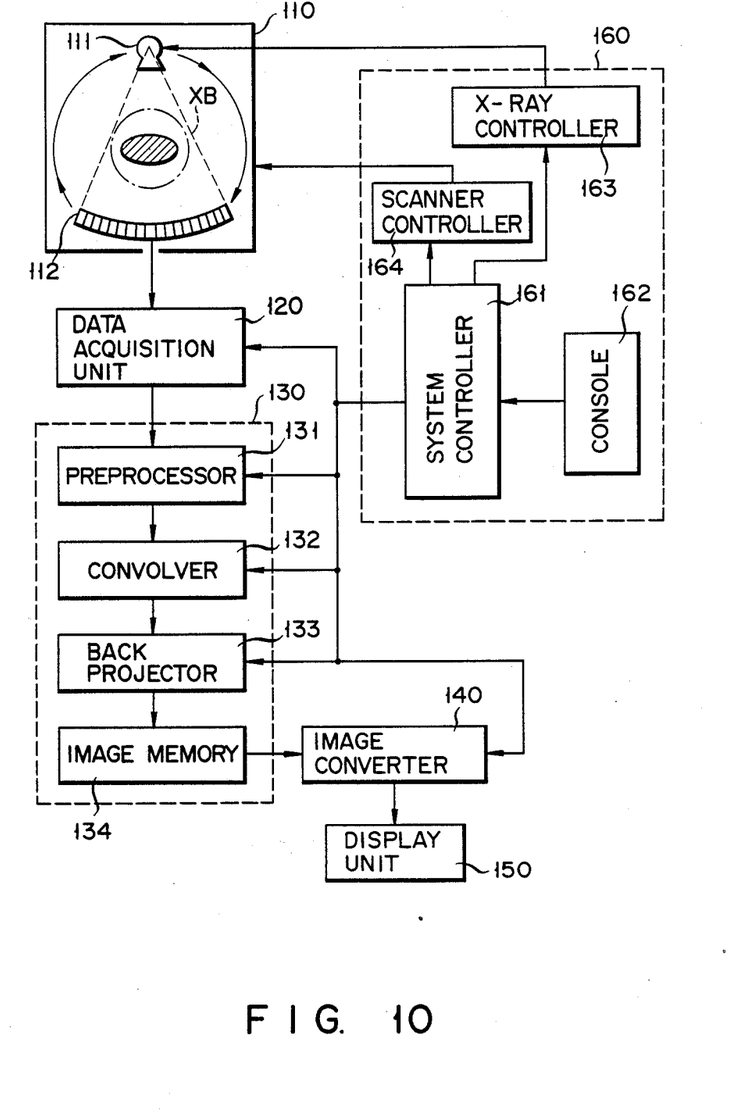
FIG. 10 is a view showing an arrangement of an X-ray CT apparatus.

When the tomographic image is obtained by the X-ray CT apparatus, as shown in FIG. 10, unlike the conventional case, the space for the marker member needs not be sufficiently assured between the tomographic image and the peripheral edge of the screen. The magnification can be larger than that of the conventional case. The tomographic image can be displayed in a large size. The positions of the marker image can be accurately read, the frame coordinate system can be accurately reconstructed, and hence the coordinates of the surgical target can be accurately calculated.

BRIEF DESCRIPTION OF THE DRAWINGS

FIGS. 1 and 2 show a conventional stereotactics apparatus, in which

FIGS. 11 and 12 show images obtained by the X-ray CT apparatus, in which

DETAILED DESCRIPTION OF THE PREFERRED EMBODIMENTS

FIGS. 4 to 8 show an embodiment of a stereotactics apparatus utilizing an MRI apparatus.

Figure 4:
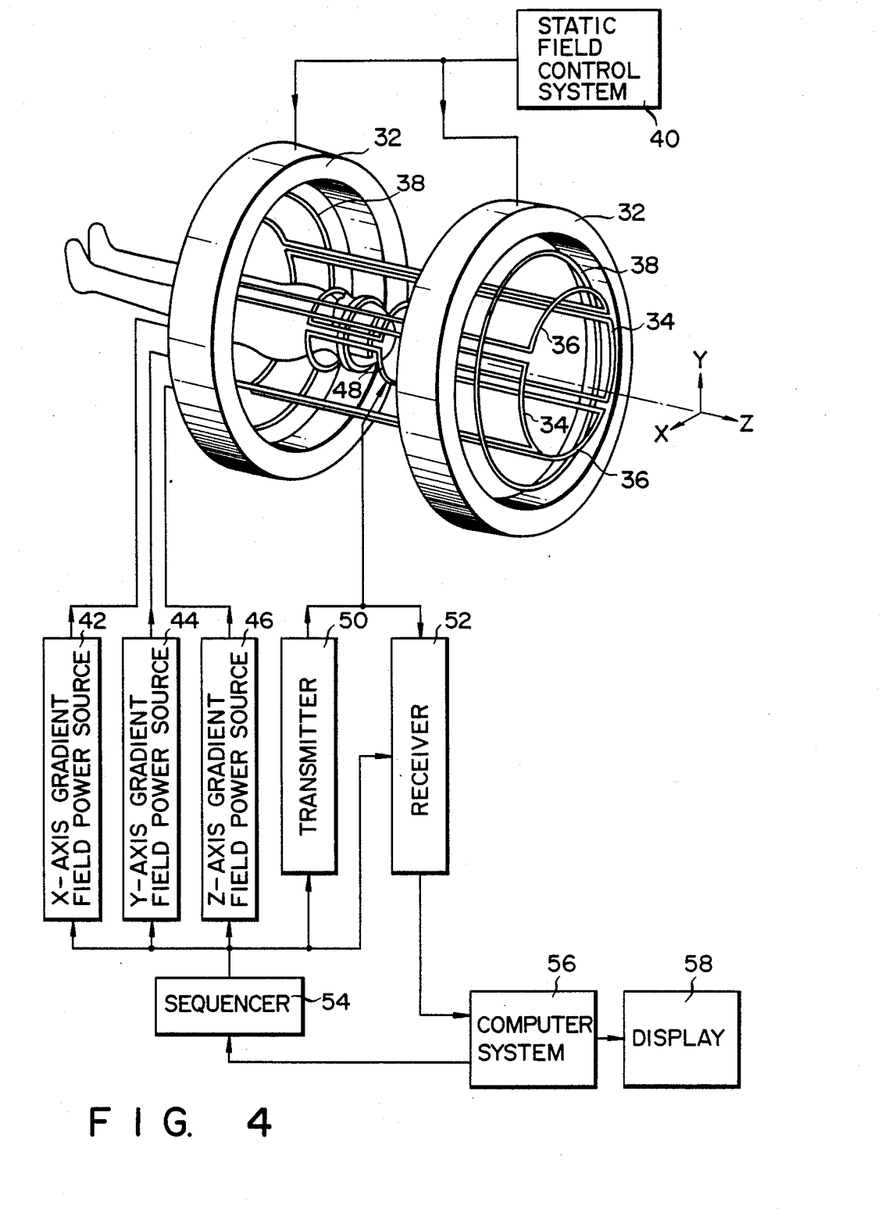
FIG. 4 is a view showing an arrangement of an MRI apparatus.

As shown in FIG. 4, an MRI apparatus comprises a pair of static field generation coils 32 for generating a uniform magnetic field. X-axis gradient field generation coil 34, Y-axis gradient field generation coil 36, and Z-axis gradient field generation coil 38 are arranged inside the pair of static field generation coils 32. Static field generation coils 32 are connected to static field control system 40. X-axis gradient field generation coil 34, Y-axis gradient field generation coil 36, and Z-axis gradient field generation coil 38 are connected to X-, Y-, and Z-axis gradient field power sources 42, 44, and 46, respectively. A point of zero intensities of the X-, Y-, and Z-axis gradient fields is defined as the center of the magnetic field.

The MRI apparatus comprises transmission/reception coil 48 for transmitting a signal for generating a rotary magnetic field and detecting an induced magnetic resonance signal. Coil 48 is connected to transmitter 50 for supplying a transmission signal and receiver 52 for receiving a detection signal. X-, Y-, and Z-axis gradient field power sources 42, 44, and 46, the transmitter 50, and the receiver 52 are connected to and are driven by a desired pulse sequence by sequencer 54. Sequencer 54 and receiver 52 are connected to computer system 56 for controlling the overall operation of the system and processing signals. Computer system 56 is connected to display 58 for displaying a tomographic image.

The head of a patient is placed in a uniform static field generated by static field generation coils 32. In this state, X-, Y-, and Z-axis gradient fields generated by X-, Y-, and Z-axis gradient field generation coils 34, 36, and 38 are superposed on the static field. At the same time, transmitter 50 is driven by a pulse sequence upon operation of sequencer 54. For example, 90°- and 180°-pulses constituting a rotary magnetic field from transmission/reception coil 48 are applied to the head of the patient. A magnetic resonance signal is generated in the brain of the patient. The induced magnetic resonance signal is detected by transmission/reception coil 48. The detected signal is fetched by computer system 56. Image reproduction is performed by computer system 56. More specifically, the detection signal is Fourier-transformed to obtain image formation of a slice of the patient. This image information is converted into a video signal, and a tomographic image is displayed on display 58.

Figure 5:
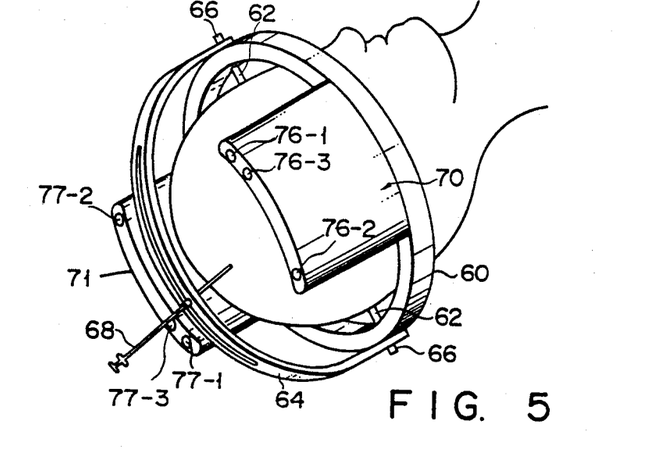
FIG. 5 is a perspective view of a stereotactics apparatus according to an embodiment of the present invention.
Figure 7:
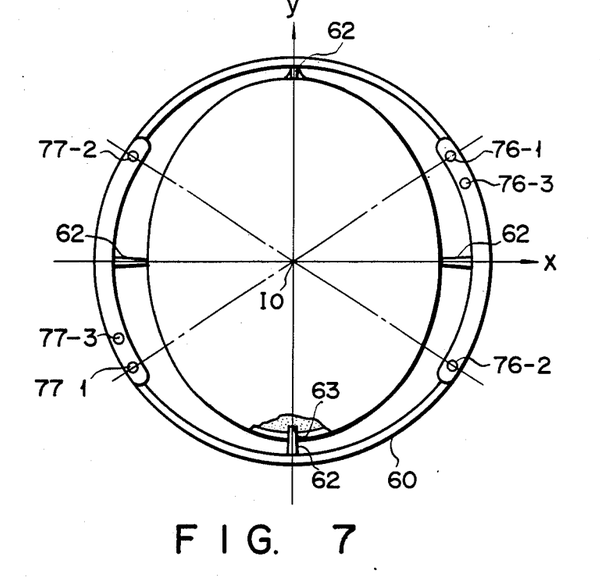
FIG. 7 is a front view of the stereotactics apparatus in FIG. 5.

As shown in FIG. 5, the stereotactics apparatus comprises annular frame 60. Frame 60 consists of a nonmagnetic material. Frame 60 is fixed to the head by a plurality of pins 62. These pins 62 are mounted in frame 60 by, e.g., threadably engaging means. The distal ends of pins 62 abut against recesses 63 formed on the skull (FIG. 7). Even if the patient is moved during the operation, frame 60 will not be removed from the head.

An operational tool consisting of probe 68 and a semicircular arc member 64 for positioning probe 68 is mounted on annular frame 60. Arc member 64 is pivotally mounted on shafts 66. Probe 68 is inserted in a groove formed in arc member 64. Arc member 64 is pivoted, probe 68 is positioned on the surgical target, and the probe is inserted into the surgical target.

Figure 6:
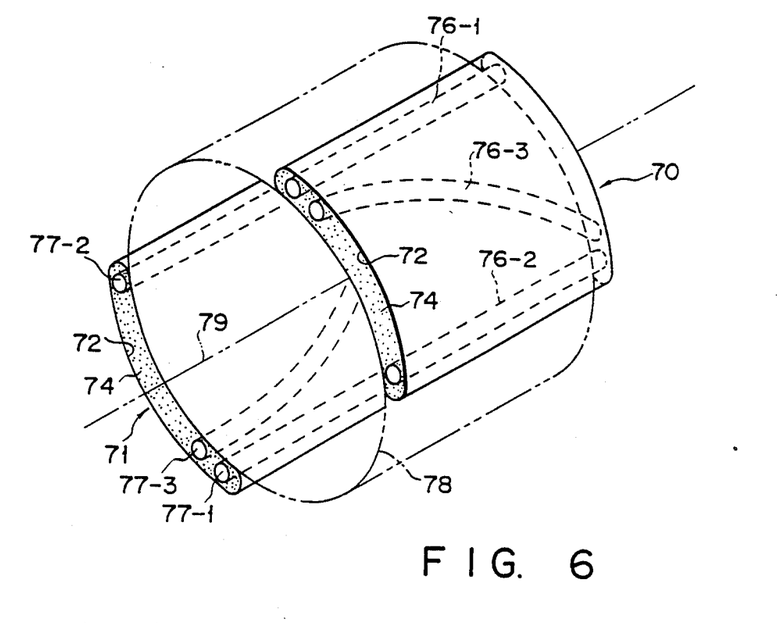
FIG. 6 is a perspective view showing gauge receptacles arranged in the stereotactics apparatus in FIG. 5.

Gauge receptacles 70 and 71 are mounted on frame 60. As shown in FIG. 6, gauge receptacles 70 and 71 comprise bags 72, marker members 76 (76-1, 76-2, and 76-3) and 77 (77-1, 77-2, and 77-3) arranged in bags 72 and consisting of, e.g., glass which does not allow generation of magnetic resonance signals, and fillers (e.g., oils and fats) 74 filled in bags 72 and allowing strong generation of the magnetic resonance signals, respectively. Note that the marker member may consist of a material which allows strong generation of the magnetic resonance signal. In this case, filler 74 consists of a material which does not allow generation of the magnetic resonance signal. In other words, one of the marker member and the filler serves to generate the magnetic resonance signal.

Gauge receptacles 70 and 71 are formed to have a concave shape toward the head side, as shown in FIG. 6. More specifically, marker members 76 and 77 are placed on an imaginary curved surface having a concave shape toward the head side. Curved imaginary plane 78 has a predetermined radius with respect to axis 79 extending in the Z direction of the gradient field. Marker members 76-1, 76-2, 77-1, and 77-2 are parallel to each other. Other marker members 76-3 and 77-3 are spirally arranged along imaginary curved surface 78.

A method of calculating coordinates of a surgical target will be described below.

As shown in FIG. 7, the stereotactics apparatus has frame coordinate system (x,y,z) defined on frame 60. A surgeon inserts probe 68 into a surgical target on the basis of coordinates $(x_0, y_0, z_0)$ of the surgical target in the frame coordinate system. The frame coordinate system is defined, as shown in FIG. 7. An intersection between a line connecting marker member 76-1 and marker member 77-1 and a line connecting marker member 76-2 and marker member 77-2 is defined as origin $I_O$ of the frame coordinate system. The x-axis extends from origin $I_O$ toward the side of the head. The y-axis extends from origin $I_O$ toward the face of the patient. The z-axis is set as a body axis of the patient from origin IO.

Figure 8:
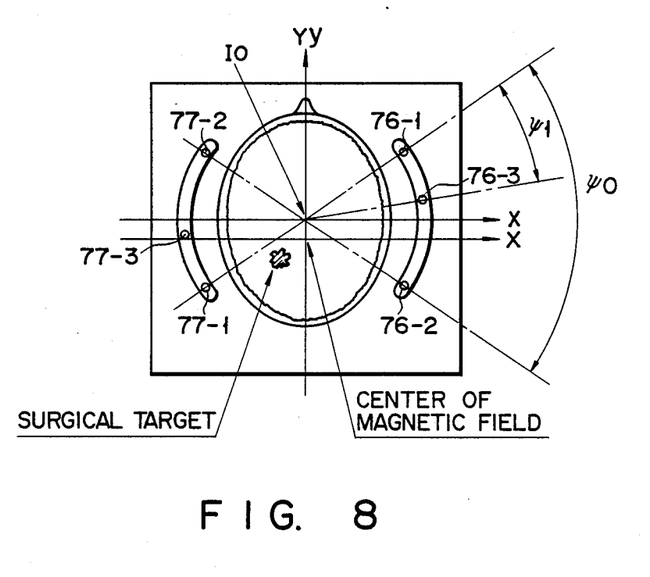
FIG. 8 is a view showing an image including a tomographic image of a head and marker images, both of which are obtained by the MRI apparatus.

As shown in FIG. 8, a tomographic image of the head is photographed by an MRI apparatus and displayed as an image. This image has image coordinate system (=gradient field coordinate system) (X,Y,Z). For this reason, coordinates $(X_0, Y_0, Z_0)$ of surgical target T in the image coordinate system are calculated on the basis of the tomographic image. However, the image coordinate system does not match the frame coordinate system. For this reason, the correspondence between the two coordinate systems must be established. More specifically, the frame coordinate system must be obtained on the image. For this purpose, marker members 76 and 77 are utilized.

Marker members 76 and 77 ar tomographically imaged together with the head and are displayed as marker images 76 and 77 together with the tomographic image of the head. The positional relationship between the marker images and the tomographic image of the head is the same as that between the head and the marker images. The frame coordinate system is reconstructed on the image on the basis of marker images 76 and 77. Origin $I_O$ of the frame coordinate system is obtained as an intersection between a line connecting marker image 76-1 and marker image 77-1 and a line connecting marker image 76-2 and marker image 77-2.

The x- and y-axes are reconstructed on the basis of a reconstructed origin $I_O$. Coordinates $(x_0, y_0)$ of the surgical target are calculated by measurement with a scale on the basis of the x- and y-axes. When the tomographic image and the marker images are displayed in a reduced size, a reduction coefficient is taken into consideration. Note that the above operations may be performed by a computer program.

Coordinate $(z_0)$ of surgical target T in the frame coordinate system is not directly obtained on the image. This coordinate is obtained as follows. Marker members 76-3 and 77-3 are spirally formed, as shown in FIG. 6. For this reason, when points on markers 76-3 and 77-3 are changed along the z-axis, the x and y values are changed. If the x and y values on marker images 76-3 and 77-3 are obtained, the z value of the slice including the surgical target can be obtained. More specifically, assume that an angle defined by marker 76-1, origin IO, and marker 76-2 is given as $\psi_0$, that an angle defined by marker 76-1, origin IO, and marker 76-3 is defined as $\psi_1$, the z-axis length of marker 76-1 or 76-2 is given as l. In this case, angle $\psi_0$ is always constant. However, when a difference between the z value of the slice and a value corresponding to the top of the head becomes small, angle $\psi_1$ is decreased. When this difference is increased, angle $\psi_1$ is increased accordingly. Therefore, the z value of the slice can be obtained by a ratio of $\psi_1$ to $\psi_0$. That is, the z value of the slice can be represented by:

$$(\psi_1/\psi_0) \cdot l$$

Coordinates $(x_0, y_0, z_0)$ of surgical target T in the frame coordinate system can be obtained as described above. The surgeon inserts probe 68 into surgical target on the basis of the above coordinates.

As described in the background of the invention, the magnetic field intensity distributions of static and gradient fields are nonuniform in the MRI apparatus. The degree of nonuniformity is increased at a position away from the center of the magnetic field. In the conventional stereotactics apparatus, as shown in FIG. 1, marker members 3 are arranged along the flat imaginary plane. For this reason, the distances between the center of the magnetic field and marker images 3-1, 3-2, and 3-3 are different from each other. A marker image which is relatively separated from the center of the magnetic field is distorted more than that close to the center of the magnetic field and is displayed with a positional error. For example, as indicated by the dotted line of FIG. 3, marker image 3-1 is distorted to result in a positional error.

To the contrary, all marker members 76-1, 76-2, 76-3, 77-1, 77-2, and 77-3 are located on curved surface 78 having a concave shape toward the head side. For this reason, all the marker members are arranged at angular positions equidistantly separated from the center of the magnetic field. As is apparent from the comparison between FIGS. 3 and 8, all the marker members according to the present invention are located relatively near the center of the magnetic field. The nonuniformity of the intensity of the magnetic field is reduced at a position nearer to the center of the magnetic field. The distortion of the marker image according to the present invention is reduced as compared with the conventional case, and the positional errors of the marker images can be suppressed. Therefore, the frame coordinate system can be accurately reconstructed on the image, and hence the coordinate of the surgical target can be accurately obtained.

As described above, the nonuniformity of the magnetic field intensity is increased at a position away from the center of the magnetic field. According to the present invention, the marker members are preferably located near the head. In addition, axis 79 of imaginary curved surface 78 along which the markers are located preferably passes through the center of the magnetic field.

The positional error of right marker image 3-1 in FIG. 3 in the conventional stereotactics apparatus is compared with a positional error of an image of marker 76-1 of the present invention. The degree of nonuniformity of the magnetic field intensity is proportional to the power of 4 to 5 of the radius from the center of the magnetic field. For this reason, the positional error of conventional marker image 3-1 is $(\sqrt{r}/r)^n = (\sqrt{2})^2$ ($n=4$ to 5) times that of marker image 3-3. However, according to the present invention, all the marker images are almost equidistantly arranged from the center of the magnetic field. For this reason, the positional errors of all marker images are almost equal to each other. According to the present invention, the positional error of marker image 76-1 can be reduced to $1/(\sqrt{2}r/2)^n = 1/(\sqrt{2})^n$ as compared with conventional marker image 3-1.

Figure 9A:
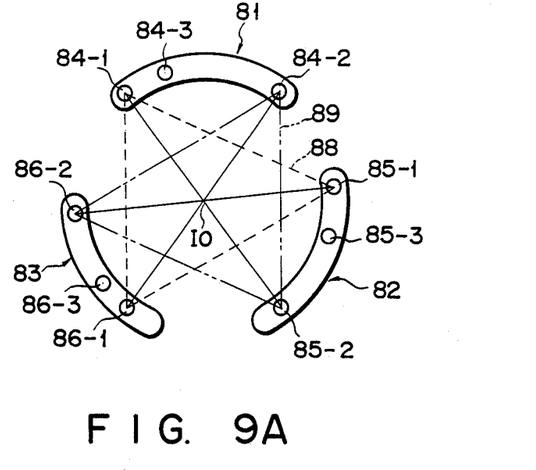
FIGS. 9A and 9B are views showing three receptacles.
Figure 9B:
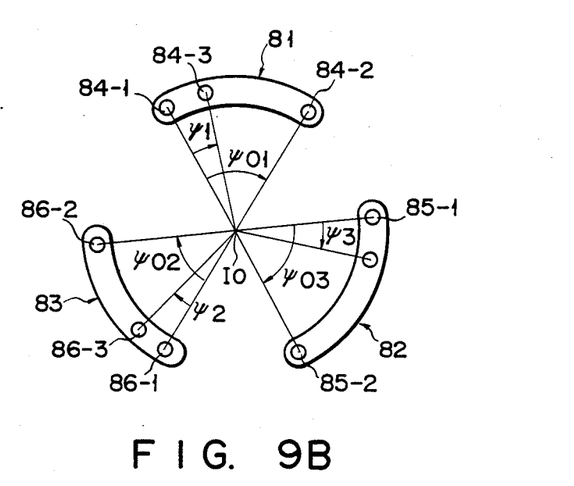

FIGS. 9A and 9B show a modification of this embodiment. The modification includes three gauge receptacles 81, 82, and 83. Marker members 84 (84-1, 84-2, and 84-3), 85 (85-1, 85-2, and 85-3), and 86 (86-1, 86-2, and 86-3) have equal radii from axis 79 and are located on curved surface 78 having a concave shape toward the head.

FIGS. 9A and 9B show three gauge receptacle images. Referring to FIG. 9A, the origin of frame coordinate system (x,y,z) is reconstructed on the screen. Marker images 84-1, 85-1, and 86-1 constitute first triangle 88. Marker images 84-2, 85-2, and 86-2 constitute second triangle 89. Origin $I_O$ of the frame coordinate system is calculated as the center of gravity of first triangle 88 or second triangle 89. Alternatively, origin $I_O$ of the frame coordinate system may be defined as an intersection of a line connecting marker images 84-1 and 85-2, a line connecting marker images 85-1 and 86-2, and a line connecting marker images 86-1 and 84-2.

Referring to FIG. 9B, coordinate $(z_0)$ of the slice in the frame coordinate system is calculated. In this same manner as in the above embodiment, $(\psi 1/\psi 01)^l$, $(\psi 2/\psi 02)^l$, and $(\psi 3/\psi 03)^l$ represent coordinate $(z_o)$ of the slice.

The number of markers in this modification is 1.5 times that of the above embodiment. For this reason, the frame coordinate system can be accurately reconstructed on the screen as compared with the above-mentioned embodiment. The coordinates of the surgical target can be accurately obtained. It is preferable that the number of markers is larger.

Figure 12:
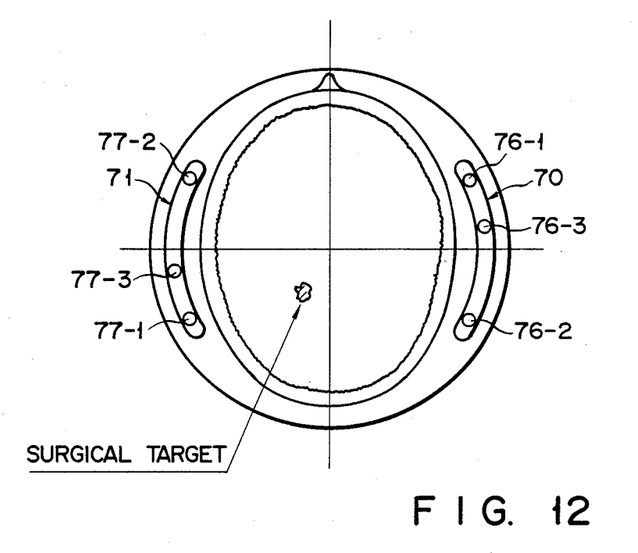

FIGS. 10 to 12 show an embodiment of the stereotactics apparatus utilizing an X-ray CT apparatus.

FIG. 10 shows a typical third-generation X-ray CT apparatus. X-ray source 111 for emitting fan beam XB and detector 112 having detector elements arranged in an arcuated shape and opposing X-ray source 111 are arranged in gantry 110. A patient is located between X-ray source 111 and detector 112. X-ray source 111 and detector 112 are rotated clockwise while X-ray source 111 opposes detector 112.

Data acquisition unit 120 integrates X-ray transmission data by detection channels of detector 112 for every X-ray path. Data acquisition unit 120 converts X-ray transmission data into a digital signal as digital projection data. The digital projection data is thus prepared for subsequent processing.

Image reconstruction unit 130 receives projection data of all directions of the patient from data acquisition unit 120 and generates a tomographic image which reflects the degree of X-ray absorption at a position of the X-ray transmission direction of the patient according to, e.g., filter correction back projection. Preprocessor 131 performs processing, such as DC component correction of the projection data, and correction of a change in X-ray intensity. Convolver 132 convolutes the projection data corrected by preprocessor 131 by using a blur recovery filter in units of projection directions and thus performs centering. Back projector 133 back-projects the projection data in image memory 134 after convolution in each direction is performed by convolver 132. A tomographic image is stored in image memory 134.

Image converter 140 converts an image in image memory 134 into a video signal representing a density image. The video signal is supplied to display unit 150. As a result, the tomographic image is displayed on the display unit.

Control unit 160 comprises system controller 161 for controlling the overall operation of the system, console 162 for allowing an operator to enter an instruction, X-ray controller 163 for controlling X-ray source 111 under the control of system controller 161, and scanner controller 164 for controlling rotation or the like of gantry 110.

In the X-ray CT apparatus, since X-ray source 111 and detector 112 are rotated, display unit 150 displays the image on a circular screen. The entire photographed area need not be displayed on the screen, and a desired region of the photographed area may be displayed on the screen. For this purpose, the image is enlarged or reduced, and the enlarged or reduced image is displayed on the screen. A two-dimensional image is constituted by a large number of small squares, i.e., pixels, whose densities are changed.

FIG. 11 shows a circular screen in which a tomographic image of the head and conventional marker images. In order to display the image with high precision, it is preferable to enlarge the image as large as possible and display the enlarged image (if the number of pixels constituting the display image is increased, the resultant image has a higher resolution). In order to reconstruct the frame coordinate system, marker images 3 must be displayed coordinate the screen. As shown in FIG. 11, the magnification of the image is set such that the marker images are located near the edge of the screen.

In a conventional stereotactics apparatus, marker members 3 are located along the flat imaginary plane. For this reason, sufficient space for the marker images must be assured between the tomographic image of the head and the edge of the screen. The magnification of the image is inevitably reduced, and the tomographic image of the head and the marker images are displayed on the screen in a relatively small size (i.e., the tomographic image of the head and the gauge images are constituted by relatively small numbers of pixels, respectively). The tomographic image of the head and the marker images cannot be displayed with a sufficiently high resolution. In addition, the sizes of the marker images displayed on the screen are relatively small (the marker image is constituted by a smaller number of pixels). The positions of the marker images cannot be accurately read on the screen. As a result, the frame coordinate system cannot be accurately reconstructed.

According to the present invention, however, marker members 76 and 77 are located on curved surface 78 having a concave shape toward the head. Unlike the conventional stereotactics apparatus, a large space for the marker images need not be assured between the tomographic image of the head and the edge of the image. For this reason, the magnification of the image in FIG. 12 is larger than that in FIG. 11. The tomographic image of the head and the marker images in FIG. 12 are displayed on the screen in a larger size as compared with those in FIG. 11 (The tomographic image of the head and the marker images are constituted by relatively larger numbers of pixels, respectively). Therefore, the tomographic image of the head and the marker images are displayed with a higher resolution. In addition, the sizes of the marker images displayed on the screen are large (i.e., the marker image is constituted by a relatively larger number of pixels). The positions of the marker images on the screen can be accurately read, and the frame coordinate system can be accurately reconstructed. Therefore, the coordinates of the surgical target can be accurately obtained.

What is claimed is:

1. A stereotactics apparatus which is adapted to utilize tomographic imaging means for photographing a predetermined portion of a patient to display a tomographic image of the predetermined portion so as to designate a surgical target of the predetermined portion on the basis of the tomographic image, comprising:
   frame means having a frame coordinate system and fixed in the predetermined portion such that the predetermined portion is located within the frame coordinate system; and
   means for calculating the coordinates of the surgical target in the frame coordinate system, said calculating means being provided with a marker member, said marker member being fixed on said frame means so that said marker member is adjacent to the predetermined portion and located within the frame coordinate system, said marker member being adapted to be tomographically imaged together with said predetermined portion by said imaging means and being adapted to be displayed as marker image together with the tomographic image of the predetermined portion, whereby the frame coordinate system is reconstructed on the basis of the displayed marker image, so that the tomographic image of the predetermined portion is located within the reconstructed frame coordinate system and coordinates of the surgical target are calculated on the basis of the reconstructed frame coordinate system,
   wherein said frame means includes a curved surface having a concave shape toward the predetermined portion, and said marker member is spirally extending along the curved surface.

2. An apparatus according to claim 1, further comprising an operational tool, fixed on said frame means, for operating the surgical target, the coordinates of which are obtained in the frame coordinate system.

3. An apparatus according to claim 1, wherein said marker member includes linearly extending rods extending along said curved surface.

4. An apparatus according to claim 1, wherein the curved surface has an axis of curvature and a substantially predetermined radius from the axis, and said marker member is located at an angular position such that all portions of the marker member are equidistantly spaced from the axis.

5. An apparatus according to claim 1, wherein said calculating means includes a gauge receptacle fixed on said frame means to store said marker member.

6. An apparatus according to claim 6, wherein said calculating means includes a plurality of gauge receptacles.

7. An apparatus according to claim 6, wherein said plurality of gauge receptacles are two symmetrical gauge receptacles.

8. An apparatus according to claim 6, wherein the curved surface has an axis and a substantially predetermined radius from the axis, and said calculating means includes three gauge receptacles located around the axis in a circumferential direction.

9. An apparatus according to claim 5, wherein said gauge receptacle stores two marker members of parallel straight rods extending along the curved surface.

10. A stereotactics apparatus which obtains a tomographic image of a predetermined portion of a patient to designate a surgical target on the basis of the tomographic image, comprising:
frame means having a frame coordinate system and fixed to the predetermined portion so that the predetermined portion is located within the frame coordinate system;
a marker member fixed to said frame means so that said marker member is adjacent to said predetermined portion and located within the frame coordinate system, and which is displayed as marker images together with the tomographic image of the predetermined portion;
tomographic imaging means for tomographically imaging said marker member together with the predetermined portion and outputting an image signal; and
means for displaying the marker image together with the tomographic image of the predetermined portion on the basis of the image signal, whereby the frame coordinate system is reconstructed on the basis of the displayed marker image, so that the tomographic image of the predetermined portion is located within the frame coordinate system, and coordinates of the surgical target are calculated on the basis of the reconstructed frame coordinate system,
wherein said frame means includes a curved surface having a concave shape toward the predetermined portion, and said marker member is spirally extending along the curved surface.

11. An apparatus according to claim 10, wherein said tomographic imaging means includes magnetic resonance imaging means for photographing the predetermined portion of the patient according to a magnetic resonance phenomenon.

12. An apparatus according to claim 11, wherein the curved surface has an axis and a substantially predetermined radius from the axis, and said marker member is located at angular position such that all portions of the marker member are equidistantly spaced from the axis.

13. An apparatus according to claim 11, wherein said calculating means includes a gauge receptacle fixed to said frame means to store said marker member, said gauge receptacle being provided with a filler for fixing said marker member therein, and said marker member is formed of a material for allowing the strong generation of a magnetic resonance signal, said filler being formed of a material which inhibits generation of a magnetic resonance signal.

14. An apparatus according to claim 11, wherein said calculating means includes a gauge receptacle fixed to said frame means to store said marker member, said gauge receptacle being provided with a filler for fixing said marker member therein, and said marker member is formed of a material which inhibits generation of the magnetic resonance signal, said filler being formed of a material for allowing strong generation of a magnetic resonance signal.

15. An apparatus according to claim 10, wherein said tomographic image imaging means includes means for CT-scanning the predetermined portion of the patient with radiation.

* * * * *